(12) United States Patent
Hely

(10) Patent No.: US 7,033,331 B1
(45) Date of Patent: Apr. 25, 2006

(54) REINFORCED WRIST BRACE WITH MULTIPLE STRAPS

(75) Inventor: John P. Hely, Oxnard, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 5 days.

(21) Appl. No.: 10/347,557

(22) Filed: Jan. 21, 2003

(51) Int. Cl.
*A61F 5/00* (2006.01)

(52) U.S. Cl. .................................. 602/21; 128/878

(58) Field of Classification Search ................ 602/5, 602/16, 20–23; 128/878, 879, 882
See application file for complete search history.

(56) References Cited

U.S. PATENT DOCUMENTS

| | | | |
|---|---|---|---|
| 2,206,404 A | 7/1940 | Jones | |
| 4,854,309 A | 8/1989 | Elsey | |
| 5,713,837 A * | 2/1998 | Grim et al. | 602/6 |
| 5,769,804 A | 6/1998 | Harris et al. | |
| 5,982,285 A | 11/1999 | Bueche et al. | |
| 6,024,715 A | 2/2000 | Maxwell | |
| 6,102,880 A * | 8/2000 | Nelson et al. | 602/21 |
| 6,190,344 B1 * | 2/2001 | Bobroff | 602/21 |
| 6,398,748 B1 | 6/2002 | Wilson | |
| 6,723,061 B1 * | 4/2004 | Williams | 602/21 |
| 2004/0049141 A1 * | 3/2004 | Slautterback et al. | 602/21 |

* cited by examiner

*Primary Examiner*—Michael A. Brown
(74) *Attorney, Agent, or Firm*—William W. Haefliger

(57) ABSTRACT

A wrist brace comprising in combination, a flexible holder to receive the user's wrist and having two flaps adapted to be closed toward one another or toward the wrist to secure the holder about the wrist of the user, tightening straps associated with the flaps, at least one first strap having an anchored end or ends at one flap and at least one second strap having an anchored end or ends at the other flap, at least one first loop on the other flap to pass at least one first strap, and at least one second loop on the other flap to pass at least one second strap, the straps and flaps having connective material thereon whereby the straps can be pulled and tightened after passing through said loops, to adjustably press-together on the connective material on the flaps.

12 Claims, 4 Drawing Sheets

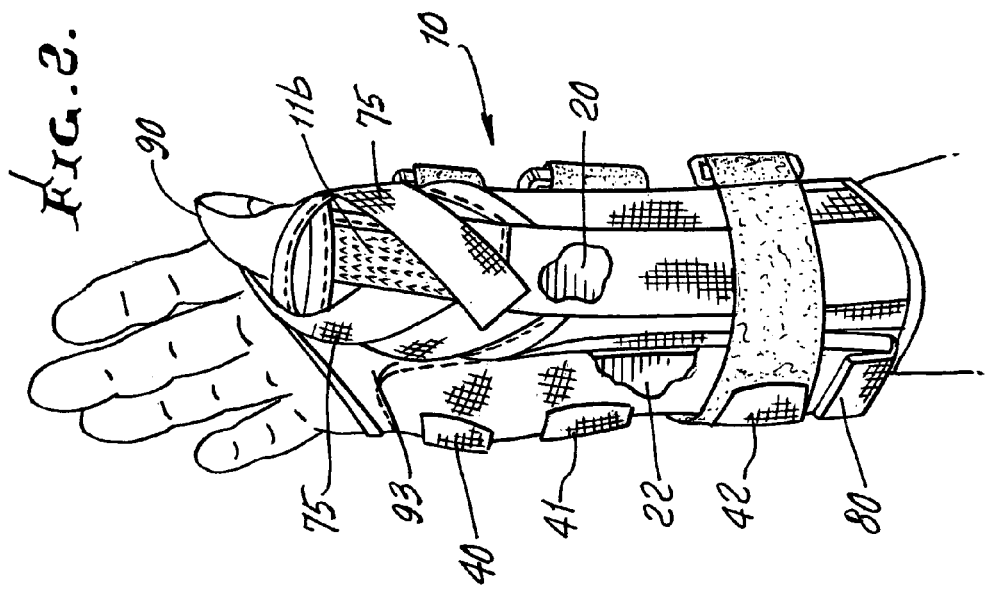
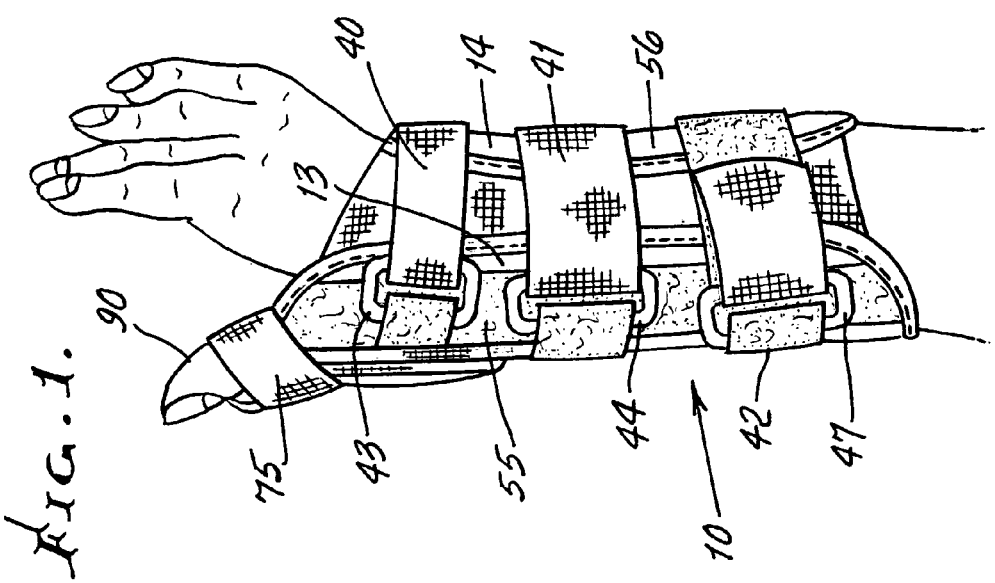

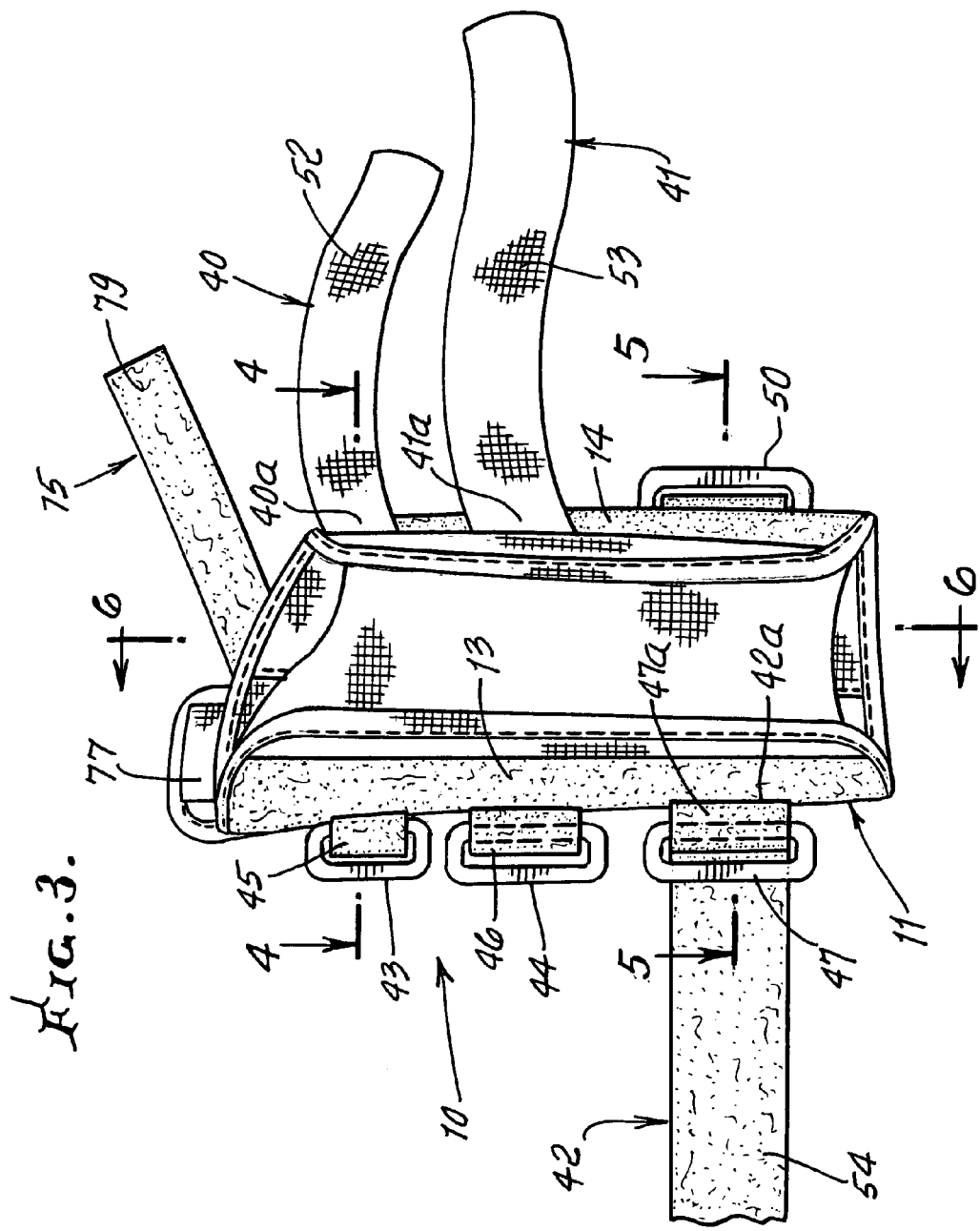

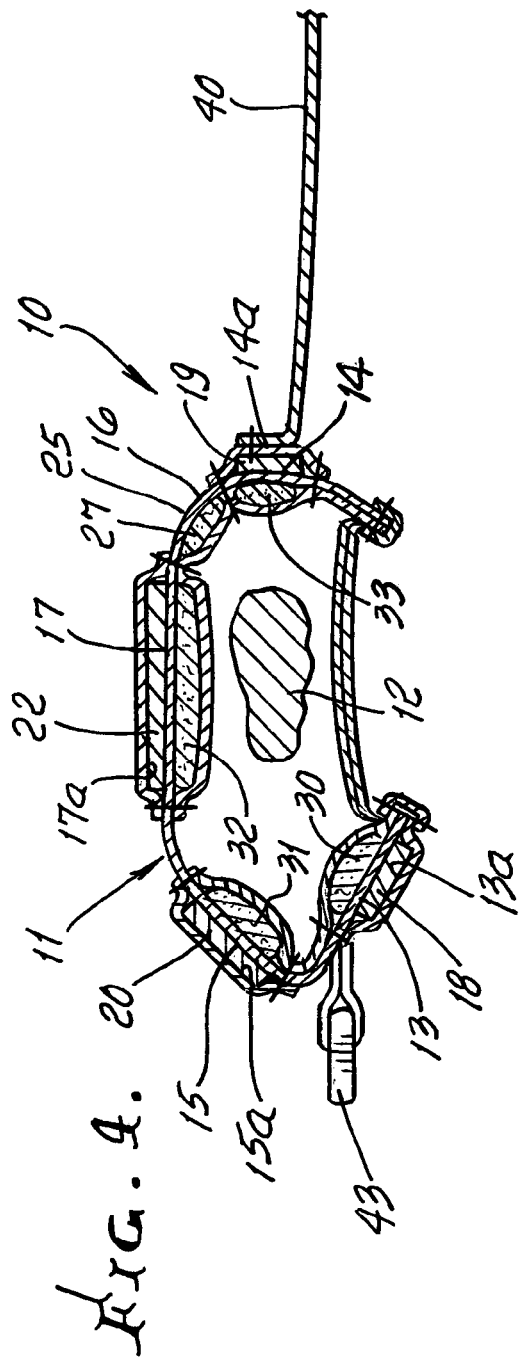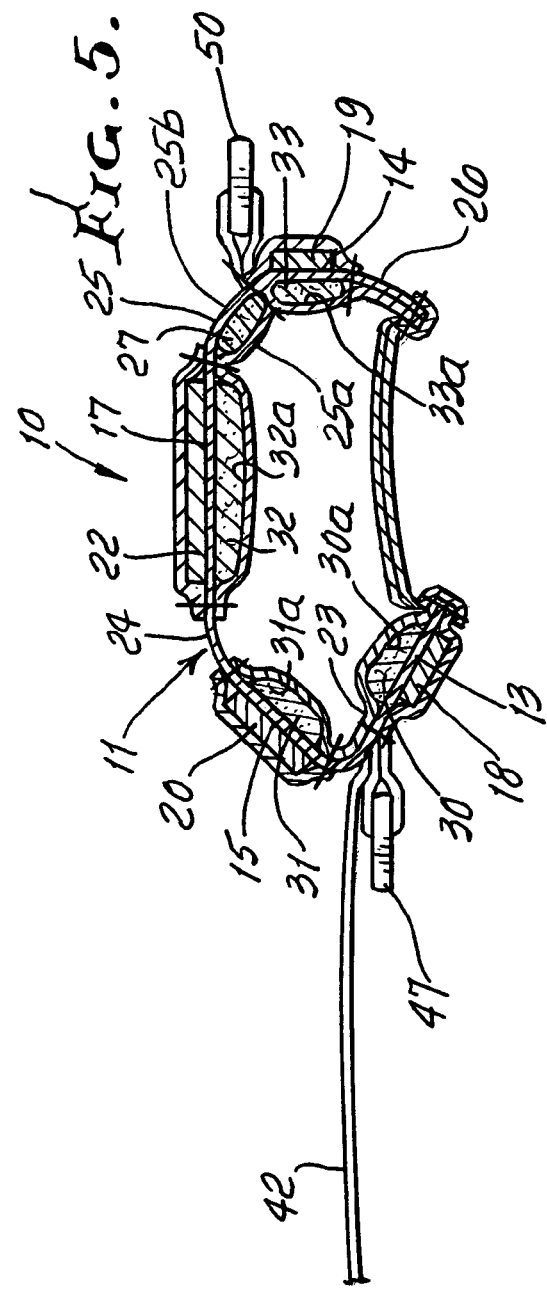

REINFORCED WRIST BRACE WITH MULTIPLE STRAPS

BACKGROUND OF THE INVENTION

This invention relates generally to wrist braces, and more particularly to improvements in strap type wrist braces.

There is need for such improvements, enabling ease of attachment to and detachment from the wrist; ease of strap wrapping and tightening with respect to the wrist holder on the brace, for flexibility of that holder, but with local stiffening to be adjustably positioned for wrist bracing in response to wrapping of multiple straps about the holder and over elongated stiffeners; and for maximum comfort to the wrist and thumb of the wearer. There is also need for an improved stiffened brace well adapted to wrists of different sizes and shapes.

SUMMARY OF THE INVENTION

It is a major object of the invention to provide an improved wrist brace meeting the above needs. Basically, the brace comprises:
 a) a flexible holder to receive the user's wrist and having two flaps adapted to be closed toward one another, or toward the wrist to secure the holder about the wrist of the user.
 b) tightening straps associated with said flaps, at least one first strap having an anchored end or ends at one said flap and at least one second strap having an anchored end or ends at the other said flap,
 c) at least one first loop on said other flap to pass said at least one first strap, and at least one second loop on said other flap to pass said at least one second strap,
 d) the straps and flaps having connective material thereon whereby the straps can be pulled and tightening after passing through said loops, to adjustably press against connective material on the flaps.

As will be seen, preferably three straps are provided at spaced locations along the holder, and may include two of the defined first straps, and one second straps.

It is another object of the invention to provide a brace wherein the anchored ends of the two first straps are attached to said one flap at two locations spaced along the length of said one flap, and the anchored end of said one second strap is attached to said other flap at a location offset from said two locations, and proximate said at least one second loop.

As will be seen, an additional loop may be attached to the one flap to also pass the one second strap.

It is a further object to provide at least one stiffener carried by at least one flap and extending lengthwise to extend beneath all three straps.

At least two such stiffeners are preferably provided to be carried by the respective two flaps, the stiffeners spaced apart about a wrist reception zone defined proximate to or by the flaps, whereby flexible flap zones are defined between the stiffeners. Four such spaced apart stiffeners are preferably provided, along with cushioning material carried by the holder to underlie said stiffeners. Provision is made for selective removal of the stiffeners to obtain desired close fit of the brace to a wrist, or greater brace flexibility.

Yet another object is to provide a flexible auxiliary strap connected to the holder to be adjustably folded over a zone between the user's thumb and forefinger, for adjustable connection to the holder, for firmly attaching the holder in lengthwise position on the wrist.

That auxiliary strap may carry connective material which press attaches to said connective material on the holder.

These and other objects and advantages of the invention, as well as the details of an illustrative preferred embodiment, will be more fully understood from the following specification and drawings, in which:

DRAWING DESCRIPTION

FIG. 1 is an elevation showing the front side of a wrist brace closed and fastened to the user's wrist;

FIG. 2 is like FIG. 1, but showing the rear or inner side of the brace overlying the user's palm;

FIG. 3 is a view like FIG. 1, but showing the brace in opened condition;

FIG. 4 is a horizontal section taken on lines 4—4 of FIG. 3;

FIG. 5 is a horizontal section taken on lines 5—5 of FIG. 3;

DETAILED DESCRIPTION

Figure 6:
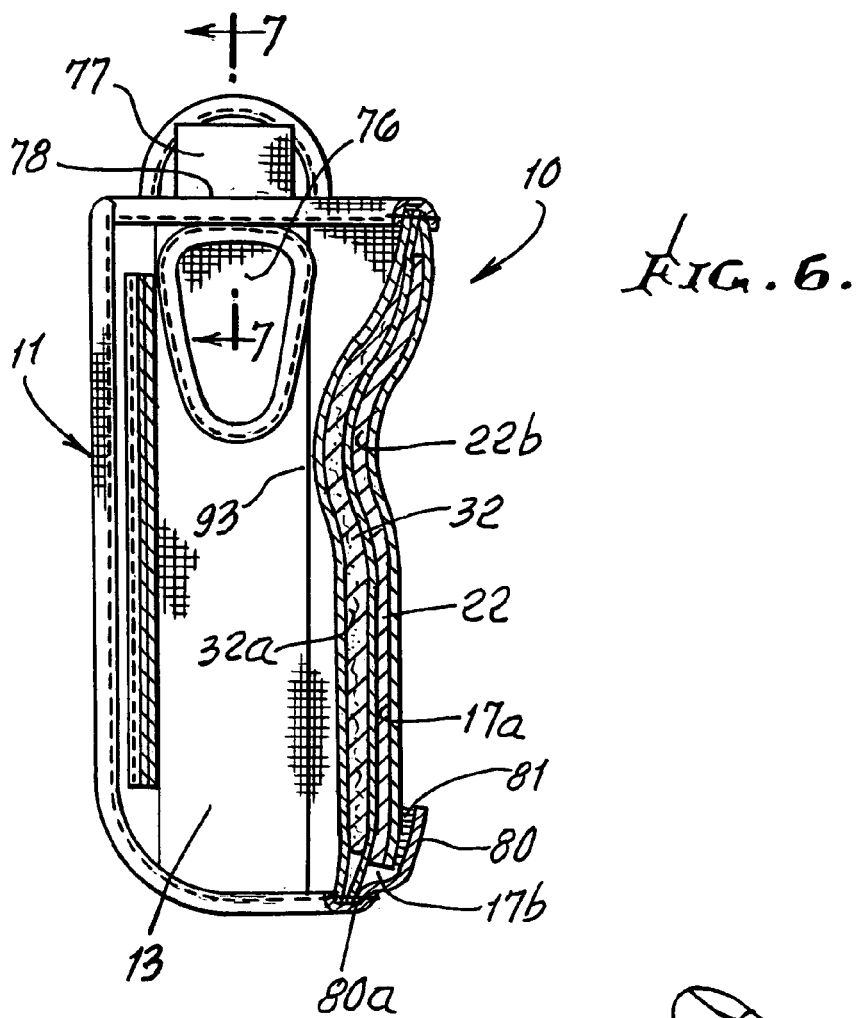
FIG. 6 is a vertical section taken on lines 6—6 of FIG. 3.

In the drawings, the illustrated wrist brace 10 includes a flexible holder 11 sized to receive the user's wrist 12. The holder includes two flaps adapted to be closed toward one another to secure the holder about wrist 12. See for example flaps 13 and 14, which are vertically elongated and extend to the front side of the holder. The flaps may alternatively be tightened toward other portions of the wrist. The holder is generally C-shaped or U-shaped in cross section as seen in FIGS. 4 and 5, and has side extents 15 and 16, and a rear extent 17. The holder may consist of flexible, durable synthetic sheet material.

Flaps 13 and 14 may typically be stiffened as by vertically elongated stiffeners 18 and 19 received in pockets 13a and 14a; holder side extent 15 may typically be stiffened as by vertically elongated stiffener 20 receive in vertically elongated pocket 15a; and holder rear extent 17 may typically be stiffened as by vertically elongated stiffener 22 received in vertically elongated pocket 17a. Such pockets and stiffeners are typically at the outer side of the holder to enhance user wrist comfort. Flexible regions or zones of the holder are shown at 23–26 in FIGS. 4 and 5, in alternation with the stiffeners pockets, and these accommodate opening and closing of the holder relative to the wrist. Regions 23–26 are vertically elongated, and region 25 defines a non-stiffened pocket between fabric layers 25a and 25b. A resiliently compressible pad 27 is received in that pocket. Preferably, resiliently compressible pads are located in pockets at the inner side of the holder fabric, opposite the stiffeners, as shown. See pad 30 in pocket 30a; pad 31 in pocket 31a; pad 32 in pocket 32a; and pad 33 in pocket 33a. Such locations of the vertically elongated pads and pockets leaves holder fabric zones 23, 24, 25 and 26 free to flex, accommodating closing about the holders wrist, despite the provision and operation of multiple stiffeners and pads.

As referred to tightening straps are associated with the flaps 13 and 14, there being at least one first strap having an anchored end or ends at one said flap and at least one second strap having an anchored end or ends at the other said flap, (see for example first straps 40 and 41 with anchored ends 40a and 41a at flap 14; and second strap 42 having an anchored end at flap 13). Also provided are:

i) at least one first loop on said other flap to pass said at least one first strap, and at least one second loop on said other flap to pass said at least one second strap, (see for example first loops 43 and 44 on flap 13 to pass a first strap 40 and to pass a first strap 41, and loop retainers 45 and 46; and see for example second loop 47 retained at 47*a* to flap 13 to pass second strap 42. An additional loop can be provided at 50 on flap 14 to pass strap 42, locating it on the holder at two locations);

ii) the straps and flaps having connective material thereon whereby the straps can be pulled and tightened after passing through such loops, to adjustably press-together on the connective material on the flaps. See connective material such as VELCRO at 52–54 on the straps, and widely dispersed at 55 and 56 on the flaps for press-on reception of material 52–54 upon fastening of the device to the wrist. FIGS. 1 and 2 show such fastening, the flaps being closed toward the wrist.

Figure 7:
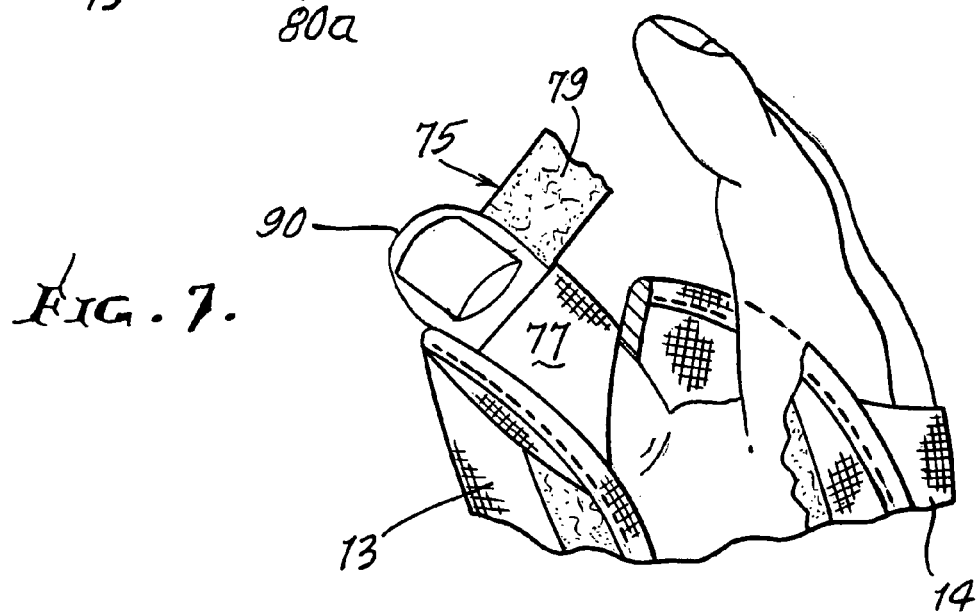
FIG. 7 is an enlarged vertical section taken on lines 7—7 of FIG. 6.

FIGS. 1 and 2 and 7 also show optional provision of a thumb strap 75 carried by the holder, to wrap about the base area of the user's thumb 90 projecting through an upper side through opening 76 in the holder, and also through a short tubular web 77 carried at the upper edge 78 of the holder. The strap 75 carries hook or pile material 79 to enable strap attachment to pile or hook on the holder at 11*b*, after being wound about the thumb. FIG. 6 shows that pocket 17*a* for metallic stiffener 22 is open or openable at 17*b* near the bottom of the holder, to enable removal of that stiffener, if desired. A short cover strap 80 attached at one end 80*a* to the holder, can be folded upwardly over opening 17*b*, to close it, and VELCRO attached to the holder, at 81, for retaining the stiffener in upwardly inserted position. Stiffener 22 is lengthwise bowed at 22*b*, to fit the curvature of the user's palm at zone 93 near the thumb opening 76 location, for better adaptation to the wrist and palm configuration. Selective endwise removal of the stiffeners from their pockets is enabled, for best fit to a wrist.

It will further be noted in the example that the anchored ends of the two first straps 40 and 41 are attached to said one flap 14 at two locations 40*a* and 41*a* spaced along the length of that one flap, and that the anchored end of second strap 42 is attached to said other flap 13 at location 42*a* offset from those two locations 40*a* and 41*a*.

The loops 43, 44 and 47 are in lengthwise general alignment, and the additional loop 50 attached to said one flap 14 is adapted to also pass said one second strap. See FIGS. 1 and 2 and the strap and loop tightening configuration. At least one stiffener, as referred to, is carried by at least one flap and extends lengthwise to extend beneath all three straps. Preferably, at least two such stiffeners are carried by the holder, extending lengthwise thereof, such stiffeners spaced apart about a wrist reception zone defined by the flaps, whereby flexible flap zones are defined between the stiffeners, as referred to. The stiffeners extend beneath all three straps, and cushions, as seen in FIGS. 1 and 2. The stiffeners are typically metallic. More specifically, there are preferably four of said stiffeners, there being cushioning material underlying all said stiffeners, to cushion tightening of the brace about the user's wrist as referred to above.

It will further be noted that the first and second straps 40, 41 and 42 have adjusted wrap around connection to the holder, in spaced relation to the auxiliary strap 75 when that auxiliary strap is adjustably connected to said connective material on the holder, or on the outer side of strap 40.

Finally, it will be noted that the outer sides of the straps may carry hook or pile material to attach to pile or hook material on the inner sides of strap end extents, folded through and over the loops, as shown.

I claim:

1. A wrist brace comprising in combination
   a) a flexible holder to receive the user's wrist and having two flaps adapted to be closed toward one another or toward the wrist to secure the holder about the wrist of the user,
   b) tightening straps associated with said flaps said tightening straps including, at least one first strap having an anchored end or ends at one said flap and at least one second strap having an anchored end or ends at the other said flap,
   c) at least one first loop on said other flap to pass said at least one first strap, and at least one second loop on said other flap to pass said at least one second strap,
   d) the straps and flaps having connective material thereon whereby the straps can be pulled and tightened after passing through said loops, to adjustably press-together on the connective material on the flaps,
   e) a flexible auxiliary thumb strap connected to the holder and adjustably folded over a zone between the user's thumb and forefinger, and adjustably connected to the holder, in overlying relation to stiffening structure carried by one of said flaps, for firmly attaching the holder in lengthwise position on the wrist,
   f) and wherein the auxiliary strap also carries connective material which press attaches to said connective material on the holder,
   g) and wherein the first and second straps have adjusted wrap around connection to the holder, in spaced relation to the auxiliary strap, when said auxiliary strap is adjustably connected to said connective material on the holder at a region tightened by one of the first and second straps,
   h) and wherein the holder is a C-shaped holder consisting of flexible sheet material, the holder sized to fit about the wrist, there being multiple stiffeners received in pockets on the holder and extending lengthwise of the holder said cushioning pads are located in holding means which are attached to the inner surface of said flexible sheet material of said holder, and cushioning pads carried by the holder in substantially longitudinally overlapping alignment with the stiffeners, the holder defining flexible zones between successive stiffeners and associated pockets, and said straps carried by the holder to wrap about the pockets and flexible zones for retaining the holder and stiffeners in affixed and adjusted condition to the wrist of the user.

2. The combination of claim 1 wherein there are two of said first straps and one second strap.

3. The combination of claim 2 wherein the anchored ends of the said two first straps are attached to said one flap at two locations spaced along the length of said one flap, and the anchored end of said one second strap is attached to said other flap at a location offset from said two locations, and proximate said at least one second loop.

4. The combination of claim 3 wherein said loops are in lengthwise alignment.

5. The combination of claim 3 including an additional loop attached to said one flap to also pass said one second strap.

6. The combination of claim 3 wherein said multiple stiffeners include at least two stiffeners carried by the respective two flaps, and extending lengthwise thereof, said stiffeners spaced apart about a wrist reception zone defined by the flaps, whereby flexible flap zones are defined between or proximate to the stiffeners.

7. The combination of claim 6 wherein said stiffeners are metallic.

8. The combination of claim 6 wherein there are four of said stiffeners.

9. The combination of claim 1 wherein said multiple stiffeners include at least one stiffener carried by at least one flap and extending lengthwise to extend beneath all three straps.

10. The combination of claim 9 wherein said at least one stiffener is bowed, lengthwise, and retained in a pocket defined by the holder, in inserted position.

11. The combination of claim 1 wherein the flexible holder has U-shape cross-section.

12. The brace of claim 1 whereas there are at least three of said tightening straps.

* * * * *